(12) United States Patent
Lipi

(10) Patent No.: US 6,383,499 B1
(45) Date of Patent: May 7, 2002

(54) TOPICAL MEDICAMENT FOR THE TREATMENT OF PSORIASIS

(75) Inventor: Ramon Efrain Vasquez Lipi, Lujan-Mendoza (AR)

(73) Assignee: Curacid America Corporation, Washington, DC (US)

( * ) Notice: Subject to any disclaimer, the term of this patent is extended or adjusted under 35 U.S.C. 154(b) by 0 days.

(21) Appl. No.: 09/792,067

(22) Filed: Feb. 26, 2001

Related U.S. Application Data

(63) Continuation of application No. 08/959,293, filed on Oct. 24, 1997, which is a continuation of application No. 08/623,709, filed on Mar. 29, 1996, now abandoned.
(60) Provisional application No. 60/008,123, filed on Oct. 30, 1995.

(51) Int. Cl.$^7$ ................................................ A61K 31/74
(52) U.S. Cl. ...................... 424/308; 560/66; 560/252; 560/254; 560/255
(58) Field of Search ............................ 424/78.02, 308; 560/66, 252, 254, 255

(56) References Cited

FOREIGN PATENT DOCUMENTS

WO          92/03142     *    3/1992

* cited by examiner

*Primary Examiner*—Terressa M. Boykin
(74) *Attorney, Agent, or Firm*—Rothwell, Figg, Ernst & Manbeck, p.c.

(57) ABSTRACT

A topical medicament for the treatment of psoriasis comprises metallic iodine, virgin wax, a variety of oils of animal and plant origin, camphor, chlorophyll and benzoic acid in a pharmaceutically acceptable emollient excipient base.

4 Claims, No Drawings

TOPICAL MEDICAMENT FOR THE TREATMENT OF PSORIASIS

CROSS REFERENCE TO PROVISIONAL APPLICATION

This application is a continuation of 08/959,293 Oct. 24, 1997 which is a continuation of 08/623,709 Mar. 29, 1996 which is abandoned related to provisional application Ser. No. 60/008,123, filed Oct. 30, 1995.

FIELD OF THE INVENTION

The present invention relates to a topical medicament for treating psoriasis.

BACKGROUND OF THE INVENTION

Psoriasis is a common chronic skin disease whose cause is unknown. It is characterized by persistent patches of redness covered with scales. The disease is, in part, determined by a genetically dominant trait. While it is absent at birth, it can begin at any age from childhood to extreme old age. Psoriasis does not, however, appear to be a communicable disease and there are no known causative factors for it in the environment.

In the involved patches, the cells of the epidermis grow and multiply many times faster than normal. The agents currently used for treatment of psoriasis include ultraviolet light, coal tar, ammoniated mercury, anthralin, and topical corticosteroids. Methotrexate has been used to treat psoriasis by systemic administration, but such treatment method is accompanied by all the side effects commonly encountered with its use for other conditions. Antimetabolite drugs such as aminopterin, thioguanine, and azaribine have also been used in treating this disease. Systemic corticosteroids or anti-malarial drugs such as chloroquine may aggravate psoriasis by mechanisms that are not understood. A low relative humidity also aggravates the disease, probably by allowing desiccation of the skin and irritation.

Improvements in the treatment of psoriasis continue to be sought. A topical medicament which is both (1) highly effective in treating the skin lesions which characterize psoriasis and is (2) based upon natural ingredients would be highly desirable.

SUMMARY OF THE INVENTION

The present invention provides a topical medicament for the treatment of psoriasis comprising as primary ingredients one or more of the following: cod liver oil, castor oil, peanut oil, olive oil, virgin wax, lanolin, metallic iodine, camphor, chlorophyll and benzoic acid. The medicament further comprises an excipient that is medically suitable for topical application to the skin.

Additional features and advantages of the invention will be set forth in the description which follows and will be apparent from the description or may be learned by practice of the invention.

DESCRIPTION OF THE PREFERRED EMBODIMENTS

Reference will now be made in detail to the presently preferred embodiments of the invention. The present invention provides a topical medicament, useful for the local treatment of the cutaneous manifestations of psoriasis, comprising a mixture of one or more of natural oils, metallic iodine, camphor, benzoic acid, virgin wax and other natural substances that act as emollients and that possess keratoplastic and keratolytic properties.

In a preferred embodiment, the present invention provides a topical medicament for the treatment of psoriasis comprising cod liver oil, castor oil, peanut oil, olive oil, virgin wax, lanolin, metallic iodine, camphor, chlorophyll, benzoic acid, and an excipient which is suitable for topical application to the skin and which, preferably, provides emollient properties. The topical medicament of the invention advantageously functions to remove the corneal layer of the epidermis, diminish the thickness of hyperkeratotic lesions, decreases inflammation and burning, and reduce capillary dilation and intercellular edema. As a result, the symptoms of psoriatic skin lesions are seen to be diminished, and the skin is allowed to recover its normal characteristics.

Metallic iodine, camphor, and benzoic acid can be characterized as inorganic antiseptics. Metallic iodine is an antiseptic agent for local (topical) use, and may be obtained from a variety of well-known sources such as igneous rock and sea water. It exhibits germicidal action in general, and fungicidal action in particular. Its germicidal action results from its combination with bacterial proteins, causing precipitation. Its action is very fast, taking place in about 10 seconds, but it combines with and is inactivated by organic substances. For example, when brought into contact with serum, blood or tissue matter, metallic iodine precipitates proteins and is partially transformed to inactive iodides. Therefore, metallic iodine has weak antiseptic action on wounds.

Moreover, at low concentrations, metallic iodine is non-toxic to tissues.

Cod liver oil is the oil obtained from the fresh livers of *Gadus morrhua* and other species of Gadidae.

The oil is extracted from the liver using steam, which breaks down the cellular membranes. Once obtained it is frozen and filtered to separate the stearin. Cod liver oil contains predominantly glycorides With non-saturated fatty acids that together comprise morrhuic acid. It also contains cholesterol, but the most important constituents are vitamins A and D, i.e., retinol and cholecalciferol or vitamin $D_3$.

Castor oil is the cold-drawn oil of the seeds, stripped of the episperm, of *Ricinus comunis* and other members of its family Euphorbisceae. It is a slightly yellow to colorless thick, viscous liquid with mild odor or odorless and subtle taste. The term peanut oil as used herein refers to the oil obtained from one or more varieties of *Arachis hypogaea*.

Camphor belongs to the category of analeptics and is recognized as a topical anti-infective and anti-pruritic agent. Camphor is also known as 2-bornanone, a dextrogyrous ketone ($C_6H_6CO$) obtained from the camphor tree, *Cinnamomum camphora T. Nees* and Ebermeier (Lauraceae). It is purified by sublimation (natural camphor) or produced synthetically (synthetic camphor) and contains no less than 96% $C_{10}H_{16}O$.

Chlorophyll is the green pigment found in plants, trees, and algae which contains chlorophyll A and B in an approximate ratio of 3:1. Chlorophyll A ($C_{55}H_{72}MgN_4O_5$, R=$CH_3$) and B ($C_{55}H_{70}MgN_4O_6$, R=CHO) are present in waxen blue-black microcrystals.

Benzoic acid is a keratolytic agent (i.e., an agent capable of reducing the normal thickness of the stratum corneum of the skin) found in various plants in free form and in combination, especially in resins and balsams. In high concentrations benzoic acid causes inflammation with erythema, some exudation and intraepidermic edema (Malpighi stratum) with epithelial break-up, followed by sloughing of the stratum corneum and peeling or exfoliation. In addition, there is a direct action on the keratin, with disintegration of the molecule. "Virgin wax" is the product of fusion and purification of the honeycomb of the *Apis mellifera* (Apidae) bee after the honey has been separated.

The excipients used in the topical medicament of the present invention can vary widely and are comprised primarily of emollients. Emollients are lipids or substances with a similar consistency which, when applied to the skin, protect and soften the skin, making it more supple. Emollients are used primarily as the excipients and bases of ointments and other dermatological preparations. A simple classification of emollients is as follows:

| Emollients as ointments | 1) Oil-based | Hydrocarbons Animal fats Vegetable oils Waxes | Eg: Petroleum Jelly eg: Castor oil Peanut oil |
|---|---|---|---|
| | 2) Absorbent bases | Cholesterol Lanolin Cetyl alcohol Stearyl alcohol | eg: sperm oil |
| | 3) Emulsive bases | Sulfated alcohols Synthetic surface-active agents Acid soaps | |
| | 4) Water-soluble bases | Basic soaps eg. Glycerine | eg: Stearic acid |

1) Oil-based: Oil-based emollients include fats. These products are anhydrous, do not absorb water and are insoluble in it, and are non-washable. Oil-based emollients include: a) hydrocarbons or mineral fats obtained by the distillation of petroleum (petroleum jelly); b) vegetable oils and liquid triglycerides; c) animal fats or solid natural triglycerides; and d) waxes or solid ethers of fatty acids and organic alcohols.

2) Absorbent bases: These bases are anhydrous and insoluble in water, and are hydrophilic. They typically form water-like emulsions in oil and, thus, can incorporate substances in aqueous solutions. In addition, they are largely non-washable. Absorbent bases include: a) Lanolin or wool fats that are obtained from sheep's wool and made up of fatty acids and cholesterol esters; and b) cetyl and stearyl alcohols, which are solid alcohols obtained by hydrogenation of their respective acids.

3) Emulsive bases: These bases absorb water, but are insoluble in it, forming water emulsions in oil that are not very washable and can be easily removed from the skin. They include surface active agents (surfactants) which improve wetting of surfaces. They include: a) soaps or salts of fatty acids that may be acidic or basic depending on whether the lipophilic group is anionic or cationic; b) sulfated alcohols which are semi-synthetic substances; and c) synthetic surface active agents.

4) Water soluble bases: These bases are anhydrous, absorb water, and are completely soluble in water. They are also non-fatty and washable. For example, glycerine is obtained from fats and, due to its hydrophobicity, has the property of extracting water from the surface of the mucosa or denuded skin. It does not damage intact skin.

When applied to the skin, these substances, which are in general chemically inert, have a protective and emollient action. The protective action occurs on healthy and diseased skin and prevents the effects of chemical, mechanical, and physical (cold, wind) irritants while decreasing burning and pruritus and producing an anti-inflammatory effect. Since these substances form a more or less impermeable layer over the skin, they prevent drying of the epidermis over the stratum corneum by decreasing the evaporation of water from the cutaneous surface. Thus, the skin is softer and more supple. In this way, emollients mimic the natural sebaceous layer that covers normal skin. The bases envisioned for use in the present invention, including the water soluble ones, are well absorbed by the skin, but almost not at all by the epidermis or the sebaceous glands of the hair follicles.

In practicing the present invention, preferably the excipient is comprised of petroleum jelly, sperm whale oil, glycerine, stearic acid, lanolin, alcohol (e.g. isopropyl or ethyl alcohol), and distilled water. More preferably, the excipient is comprised of about 2.2% liquid petroleum jelly, about 1sperm whale oil, about 14% glycerine, about 3.5 stearic acid, about 3.0t virgin wax, about 21.0% lanolin, about 1.5% alcohol, and about 5.5% distilled water.

As used herein the term sperm whale oil refers to the waxy substance extracted from the head of the whale, Plyseter. Glycerine is obtained by hydrolysis of fats and fixed oils. Stearic acid is a mixture of solid fatty acids in variable proportions and as used herein the term virgin wax refers to the product of the melting and purification of the honeycomb of the honeybee Apis mellifera after the honey has been separated. Lanolin refers to the purified, anhydrous fat-like substance obtained from sheep's wool.

In treating a subject with the topical medicament of the present invention, the medicament, which can be in the form of either a cream or an ointment, preferably is spread on a gauze compress to be placed on the effected zone, following which a soft occlusive bandage is applied. This regimen is repeated about 3 times daily at the beginning of treatment and then less frequently as a favorable course of treatment is observed. The total time of treatment depends upon how the lesions evolve.

In light of the fact that the medicament is applied in a topical fashion, it is not typical to set maximum and minimum doses. Rather, the quantity of the medicament to be applied should be adapted to the size of the lesions. For maximum benefit, the lesions should be thoroughly covered by the medicament.

Very little, if any, of the components of medicament are absorbed by the skin. Thus, no side effects associated with the use of the topical medicament of the invention are expected.

Once prepared, the topical medicament of the invention does not require any special conditions for its preservation. The final product can be packaged in, for example, 20 g. and 50 g. tubes, or in 50 g., 100 g., 200 g. and 500 g. jars. The topical medicament of the invention has shown good clinical efficacy and capacity to remove the stratum corneum of the epidermis, diminish the thickness of hyperkeratotic lesions, inhibit inflammation, quickly relieve pruritus and burning, and reduce capillary dilation and intercellular edema, thus enabling the skin of psoriatic lesions to recover its normal characteristics.

The present invention is further described in the following Example, which is provided for illustrative purposes only and is not to be construed as limiting. All percentages, unless otherwise noted, are expressed by weight based upon the total weight of the product.

EXAMPLE 1

In order to prepare a 100 g. sample of the topical medicament of the invention, the following ingredients are combined:

PRIMARY INGREDIENTS
    Cod liver oil . . . 16.6 g
    Castor oil . . . 3.6 g
    Peanut oil . . . 19.6 g
    Olive Oil . . . 0.6 g
    Virgin wax . . . 2.0 g
    Lanolin . . . 6.0 g
    Metallic iodine . . . 0.1 g
    Camphor . . . 0.1 g
    Chlorophyll . . . 0.65 g
    Benzoic acid . . . 0.05 g EXCIPIENT BASE
    Petroleum jelly . . . 2.2 ml
    Sperm whale oil . . . 1.0 g
    Glycerine . . . 14.0 g
    Stearic acid . . . 3.5 g
    Alcohol . . . 1.5 ml
    Distilled water . . . 5.5 ml Preparation Step 1

The total quantities of the following ingredients are placed in an appropriate container: stearic acid, virgin wax, petroleum jelly (or other medically acceptable excipient), lanolin, and sperm whale oil. The ingredients are heated to 65° C.–70° C. in a water bath and mixed continuously until the solid phase melts.

Preparation Step 2

The peanut oil, olive oil, castor oil, cod liver oil, camphor, and benzoic acid are mixed in another appropriate stainless steel container, and shaken until homogeneity is achieved.

Preparation Step 3

A mixture of glycerine and distilled water is prepared while in another container the iodine is dissolved in alcohol. The glycerine/water mixture is added to the product obtained in Preparation Step 1.

Preparation Step 4

Once the mixture is homogeneous, the iodine, dissolved in alcohol, is added to the homogeneous mixture from Step 3, shaking continuously until the contents are uniform and homogeneous.

Preparation Step 5

The product obtained in Preparation Step 4 is added to the homogeneous mixture of Preparation Step 2, shaking constantly until the contents are uniform and homogeneous. The product then is cooled to 35C.–40C.

I claim:

1. A topical medicament for the treatment of psoriasis, comprising cod liver oil, castor oil, peanut oil, olive oil, virgin wax, lanolin, metallic iodine, camphor, chlorophyll, benzoic acid, and a pharmaceutically acceptable excipient for topical application to the skin.

2. A topical medicament for the treatment of psoriasis, consisting essentially of cod liver oil, castor oil, peanut oil, olive oil, virgin wax, lanolin, metallic iodine, camphor, chlorophyll, benzoic acid, and a pharmaceutically acceptable excipient for topical application to the skin.

3. The topical medicament of claim 1, wherein the components are present in the following proportions by weight:
    about 16.6% cod liver oil;
    about 3.6% castor oil;
    about 19.6% peanut oil;
    about 0.6% olive oil;
    about 25% virgin wax;
    about 6% lanolin;
    about 0.1% metallic iodine;
    about 0.1% camphor;
    about 0.65% chlorophyll;
    about 0.05% benzoic acid; and
    about 27.7% excipient.

4. The topical medicament of claim 2, wherein the components are present in the following proportions by weight:
    about 16.6% cod liver oil;
    about 3.6% castor oil;
    about 19.6% peanut oil;
    about 0.6% olive oil;
    about 25% virgin wax;
    about 6% lanolin;
    about 0.1% metallic iodine;
    about 0.1% camphor;
    about 0.65% chlorophyll;
    about 0.05% benzoic acid; and
    about 27.7% excipient.

* * * * *